US009259456B2

(12) United States Patent (10) Patent No.: US 9,259,456 B2
Kidron (45) Date of Patent: Feb. 16, 2016

(54) METHODS AND COMPOSITIONS FOR ORAL ADMINISTRATION OF PROTEINS

(75) Inventor: Miriam Kidron, Jerusalem (IL)

(73) Assignee: Oramed Pharmaceuticals Inc., Jerusalem (IL)

( * ) Notice: Subject to any disclaimer, the term of this patent is extended or adjusted under 35 U.S.C. 154(b) by 549 days.

(21) Appl. No.: 11/513,343

(22) Filed: Aug. 31, 2006

(65) Prior Publication Data

US 2007/0087957 A1 Apr. 19, 2007

Related U.S. Application Data

(60) Provisional application No. 60/713,716, filed on Sep. 6, 2005.

(51) Int. Cl.
| | |
|---|---|
| *A61K 38/28* | (2006.01) |
| *A61K 9/20* | (2006.01) |
| *A61K 9/28* | (2006.01) |
| *A61K 9/48* | (2006.01) |
| *A61K 31/202* | (2006.01) |
| *A61K 31/22* | (2006.01) |
| *A61K 38/56* | (2006.01) |
| *A61K 35/60* | (2006.01) |

(52) U.S. Cl.
CPC ............... *A61K 38/28* (2013.01); *A61K 9/2013* (2013.01); *A61K 9/2846* (2013.01); *A61K 9/485* (2013.01); *A61K 9/4866* (2013.01); *A61K 9/4875* (2013.01); *A61K 9/4891* (2013.01); *A61K 31/202* (2013.01); *A61K 31/22* (2013.01); *A61K 35/60* (2013.01); *A61K 38/56* (2013.01); *A61K 9/2068* (2013.01); *A61K 9/2866* (2013.01)

(58) Field of Classification Search
CPC .................................................... A61K 38/28
See application file for complete search history.

(56) References Cited

U.S. PATENT DOCUMENTS

| | | | |
|---|---|---|---|
| 4,579,730 A * | 4/1986 | Kidron et al. .................. 424/465 |
| 5,034,415 A * | 7/1991 | Rubin ............................ 514/560 |
| 5,206,219 A * | 4/1993 | Desai ............................... 514/3 |
| 5,665,700 A * | 9/1997 | Cho et al. ........................ 514/6.5 |
| 5,824,638 A * | 10/1998 | Burnside et al. ................... 514/3 |
| 6,692,766 B1 * | 2/2004 | Rubinstein et al. ........... 424/487 |
| 6,761,903 B2 | 7/2004 | Chen et al. |
| 6,858,576 B1 | 2/2005 | Young et al. |
| 2002/0032171 A1 | 3/2002 | Chen et al. |
| 2003/0118610 A1 | 6/2003 | Stern et al. |
| 2005/0143303 A1 | 6/2005 | Quay et al. |
| 2005/0232981 A1 | 10/2005 | Ben-Sasson |
| 2006/0018874 A1 | 1/2006 | Radhakrishnan et al. |
| 2006/0045868 A1 | 3/2006 | Meezan et al. |
| 2006/0045869 A1 | 3/2006 | Meezan et al. |
| 2006/0234913 A1 | 10/2006 | Arbit et al. |
| 2006/0264401 A1 | 11/2006 | Campbell et al. |
| 2006/0286129 A1 | 12/2006 | Sarubbi |
| 2006/0293232 A1 | 12/2006 | Levy et al. |
| 2007/0077283 A1 | 4/2007 | Quay et al. |
| 2007/0087957 A1 | 4/2007 | Kidron |

FOREIGN PATENT DOCUMENTS

| | | |
|---|---|---|
| CN | 101095942 A | 2/2008 |
| IL | 68769 A | 2/1986 |
| JP | 02-250823 | 10/1990 |
| JP | 09-208485 A | 8/1997 |
| JP | 10-330287 A | 12/1998 |
| JP | 00-050793 A | 2/2000 |
| JP | 2001-240558 | 4/2001 |
| KR | 01-0069433 A | 3/2001 |
| KR | 01/0069322 A | 7/2001 |
| WO | WO 91/14454 A1 | 10/1991 |
| WO | WO 97/03688 | 2/1997 |
| WO | WO 00/24424 A1 | 7/2000 |
| WO | WO 2007/002923 | 3/2007 |
| WO | WO 2009/118722 A2 | 10/2009 |

OTHER PUBLICATIONS

Sekiguchi et al. JP 2001-240558. Sep. 9, 2001. English translation obtained form the JPO webpage.*
Li et al, Oil-based formulations for oral delivery of insulin, J Pharm Pharmacol, Sep. 2004;56(9):1101-7.*
Bar-On, H., et al.; "Enteral Administration of Inslin in the Rat"; Br. J. Pharmac. (1981); 73: 21-24.
Bendayan, et al.; "Morpho-cytochemical and biochemical evidence for insulin absorption by the rat ileal epithelium"; Diabetologia (1990); 33: 197-204.
Bendayan, et al.; "Biochemical and morpho-cytochemical evidence for the intestinal absorption of insulin in control and diabetic rats. Comparison between the effectiveness of duodenal and colon mucosa"; Diabetologia (1994); 37: 119-126.
Carino, et al.; "Oral insulin delivery"; Advanced Drug Delivery Review (1999); 35: 249-257.
Cernea, et al.; "Dose-Response Relationship of Oral Insulin Spray in Healthy Subjects"; Diabetes Care (2005); 28(6): 1353-1357.

(Continued)

*Primary Examiner* — Amber D Steele
(74) *Attorney, Agent, or Firm* — Wolf, Greenfield & Sacks, P.C.

(57) ABSTRACT

This invention provides compositions comprising a protein and an omega-3 fatty acid, method for treating diabetes mellitus, comprising administering same, and methods for oral administration of a protein with an enzymatic activity, comprising orally administering same.

45 Claims, No Drawings

(56) References Cited

OTHER PUBLICATIONS

Cernea, et al.; "Dose-Response Relationship of an Oral Insulin Spray in Six Patients with Type 1 Diabetes: A Single-Center, Randomized, Single-Blind, 5-Way Crossover Study"; Clinical Therapeutics (2005); 27(10): 1562-1570.
Cernea, et al.; "Comparison of pharmacokinetic and pharmacodynamic properties of single-dose oral insulin spray and subcutaneous insulin injection in healthy subjects using the euglycemic clamp technique"; Clinical Therapeutics (2004); 26(12): 2084-2091.
Cole, et al.; "Challenges and opportunities in the encapsulation of liquid and semi-solid formulations into capsules for oral administration"; Advanced Drug Delivery Review (2008); 60: 747-756.
Iyer, et al.; "Oral insulin—a review of current status"; Diabetes, Obesity and Metabolism (2010); 12: 179-185.
Kidron, et al.; "A novel per-oral insulin formulation: proof of concept study in non-diabetic subjects"; Diabetic Medicine (2004); 21: 354-357.
Lasserson, et al.; "Optimal insulin regimens in type 2 diabetes mellitus: systematic review and meta-analyses"; Diabetologia (2009); 52: 1990-2000.
Ma, et al.; "In vitro and in vivo evaluation of a novel oral insulin formulation"; Acta Pharmacologica Sinica (2006); 27(10): 1382-1388.
Nissan, et al.; "Intestinal absorption of low molecular weight heparin in animals and human subjects"; Haemostasis (2000); 30: 225-232.
Raz, et al.; "Rectal Administration of Insulin"; Israel Journal of Medical Sciences (1984); 20: 173-175.
Ziv, et al.; "Bile Salts Promote the Absorption of Insulin from the Rat Colon"; Life Sciences (1981); 29: 803-809.
Ziv, et al.; "Absorption of Protein via the Intestinal Wall A Quantitative Model"; Biochemical Pharmacology (1987); 36(7): 1035-1039.
Ziv, et al.; "Oral administration of insulin in solid form to nondiabetic and diabetic dogs"; Journal of Pharmaceutical Sciences (1994); 83(6): 792-794.
Agarwal, et al.; "Oral Delivery of Proteins: Effect of Chicken and Duck Ovomucoid on the Stability of Insulin in the Presence of α-Chymotrypsin and Trypsin"; Pharm. Pharmacol. Commun.; (2000); 6: 223-227.
Cournarie, et al.; "Insulin-loaded W/O/W multiple emulsions: comparison of the performances of systems prepared with medium-chain-triglycerides and fish oil"; Euro. J. of Pharmaceutics and BioPharmaceutics; (2004); 58(3): 477-482.
Onuki, et al.; "In vivo effects of highly purified docosahexaenoic acid on rectal insulin absorption"; Int. J. of Pharmaceutics; (2000); 198(2): 147-156.
Silva-Cunha et al.; "W/O/W multiple emulsions of insulin containing a protease inhibitor and an absorption enhancer: preparation, characterization and determination of stability towards proteases in vitro"; Int. J. of Pharmaceutics; (1997); 158(1): 79-89.
Maher, S. et al.; "Safety and efficacy of sodium caprate in promoting oral drug absorption: from in vitro to the clinic"; Advanced Drug Delivery Reviews; (2009); 61: 1427-1449.
Li and Deng; "Oil-based formulation for oral delivery of insulin"; J. Pharmacy Pharmacol 2004; 56: 1101-1107.
Hays, et al.; "Prevention and Treatment of Type 2 Diabetes: Current Role of Lifestyle, Natural Product, and Pharmacological Interventions"; Pharmacol. Ther. (2008); 118(2): 181-191.
Gowthamarajan & Kulkarni; Oral Insulin—Fact or Fiction—Possibilities of Achieving Oral Delivery for Insulin; Resonance (2003); 38-46.
Heine, et al.; "Exenatide versus Insulin Glargine in Patients with Suboptimally Controlled Type 2 Diabetes"; American College of Physicians—Annals of Internal Medicine 2005; 143(8): 559-569.
Kidron, et al.; "Extended exposure to an oral insulin formulation yields decreased insulin secretion in Type II diabetes subjects"; Diabetes Technology Meeting Nov. 11-13, 2010.
Mack, et al. "Antiobestiy action of peripheral exenatide (exendin-4) in rodents: effects on food intake, body weight, metabolic status and side-effect measures"; International Journal of Obesity (2006); 30: 1332-1340.
Miyagawa, Jun-ichiro; Med Sci Digest 2008 34(4):147-150.
Morishita, et al.; "Hypoglycemic effect of novel oral microspheres of insulin with protease inhibitor in normal and diabetic rats"; Int. J. of Pharma; (1992); 78: 9-16.
Ray Dirks Research; "Novo Nordisk Sitting on $2 Billion in Cash May Look to Acquire Oramed or ISIS for Oral Insulin"; May 31, 2012.
Sherman, "Oramed Enrolls First Patient in its Phase 2a U.S. Oral Insulin Clinical Trial"; Jul. 8, 2013.

\* cited by examiner

METHODS AND COMPOSITIONS FOR ORAL ADMINISTRATION OF PROTEINS

CROSS-REFERENCE TO RELATED APPLICATIONS

This Application claims priority of U.S. Provisional Ser. No. 60/713,716, filed on Sep. 6, 2005, which is included in its entirety by reference herein.

FIELD OF INVENTION

This invention provides compositions comprising a protein and an omega-3 fatty acid, and a method for administering same.

BACKGROUND OF THE INVENTION

Due to improved biotechnology, the accessibility of biologically active peptides to the pharmaceutical industry has increased considerably. However, a limiting factor in the development of peptide drugs is the relative ineffectiveness when given perorally. Almost all peptide drugs are parenterally administered, although parenterally administered peptide drugs are often connected with low patient compliance.

Insulin is a medicament used to treat patients suffering from diabetes, and is the only treatment for insulin-dependent diabetes mellitus. Diabetes Mellitus is characterized by a pathological condition of absolute or relative insulin deficiency, leading to hyperglycemia, and is one of the main threats to human health in the 21st century. The global figure of people with diabetes is set to rise to 220 million in 2010, and 300 million in 2025. Type I diabetes is caused primarily by the failure of the pancreas to produce insulin. Type II diabetes, involves a lack of responsiveness of the body to the action of insulin.

Approximately 20%-30% of all diabetics use daily insulin injections to maintain their glucose levels. An estimated 10% of all diabetics are totally dependent on insulin injections.

Currently, the only route of insulin administration is injection. Daily injection of insulin is causes considerable suffering for patients. Side effects such as lipodystrophy at the site of the injection, lipatrophy, lilpohypertrophy, and occasional hypoglycemia are known to occur. In addition, subcutaneous administration of insulin does not typically provide the fine continuous regulation of metabolism that occurs normally with insulin secreted from the pancreas directly into the liver via the portal vein.

The present invention addresses the need for an alternate solution for administration of insulin.

SUMMARY OF THE INVENTION

This invention provides compositions comprising a protein and an omega-3 fatty acid, method for treating diabetes mellitus, comprising administering same, and methods for oral administration of a protein with an enzymatic activity, comprising orally administering same.

In one embodiment, the present invention provides a composition comprising an insulin protein and an omega-3 fatty acid.

In another embodiment, the present invention provides a method for oral administration of a protein with an enzymatic activity to a subject, whereby a substantial fraction of the protein retains the enzymatic activity after absorption through an intestinal mucosal barrier of the subject, comprising administering orally to the subject a pharmaceutical composition comprising the protein and an omega-3 fatty acid, thereby orally administering a protein with an enzymatic activity to a subject.

In another embodiment, the present invention provides a method for treating diabetes mellitus in a subject, comprising administering orally to the subject a pharmaceutical composition comprising insulin and an omega-3 fatty acid, thereby treating diabetes mellitus.

DETAILED DESCRIPTION OF THE INVENTION

This invention provides compositions and methods comprising a protein and an omega-3 fatty acid. In one embodiment, the protein having a molecular weight up to 200,000 Daltons. In a preferred embodiment, the protein having a molecular weight up to 100,000 Daltons. In one embodiment, the present invention further provides an enhancer which enhances absorption through the intestines.

In one embodiment, the protein is an enzyme. In some embodiments, the protein is a receptor ligand, transporter, or a storage protein. In one embodiment, the protein is a structural protein.

In some embodiments, the enzyme is an oxidoreductase, transferase, hydrolase, lyase, isomerase, or ligase. In some embodiments, oxidoreductases act on the aldehyde or oxo group of donors, on the CH—CH group of donors, on the CH—NH(2) group of donors, on the CH—NH group of donors, on NADH or NADPH, on the CH—OH group of donors, on nitrogenous compounds as donors, on a sulfur group of donors, on a heme group of donors, on diphenols and related substances as donors, on a peroxide as acceptor, on hydrogen as donor, on single donors with incorporation of molecular oxygen, on paired donors, on superoxide as acceptor, oxidizing metal ions, on CH or CH(2) groups, on iron-sulfur proteins as donors, on reduced flavodoxin as donor, on phosphorus or arsenic in donors, or on x-H and y-H to form an x-y bond.

In some embodiments, transferases are acyltransferases or glycosyltransferases. In some embodiments, transferases transfer aldehyde or ketone residues. In some embodiments, transferases transfer alkyl or aryl groups, other than methyl groups. In some embodiments, transferases transfer nitrogenous, phosphorous, sulfur or selenium containing groups.

In some embodiments, hydrolases are glycosylases or act on ether bonds, on peptide bonds, on carbon-nitrogen bonds, other than peptide bonds, on acid anhydrides, on carbon-carbon bonds, on halide bonds, on phosphorus-nitrogen bonds, on sulfur-nitrogen bonds, on carbon-phosphorus bonds, on sulfur-sulfur bonds, or on carbon-sulfur bonds.

In some embodiments, lyases are carbon-carbon lyases, carbon-oxygen lyases, carbon-nitrogen lyases, carbon-sulfur lyases, carbon-halide lyases, phosphorus-oxygen lyases, or other lyases.

In some embodiments, isomerases are racemases or epimerases, cis-trans-isomerases, intramolecular oxidoreductases, intramolecular transferases, intramolecular lyases, or other isomerases.

In some embodiments, ligases form carbon-sulfur bonds, carbon-nitrogen bonds, carbon-carbon bonds, phosphoric ester bonds, or nitrogen-metal bonds.

In some embodiments, transporter proteins are annexins, ATP-binding cassette transporters, hemoglobin, ATPases, calcium channels, potassium channels, sodium channels, or solute carriers.

In some embodiments, storage proteins comprise albumins, lactoglobulins, casein ovomucin, ferritin, phosvitin, lactoferrin, or vitellogenin. In one embodiment, albumins comprise avidin, ovalbumin, serum albumin, parvalbumin, c-reactive protein prealbumin, conalbumin, ricin, lactalbumin, methemalbumin, or transthyretin.

In some embodiments, structural proteins comprise amyloid, collagen elastin, or fibrillin.

In some embodiments, the protein is a viral protein, bacterial protein, invertebrate protein, or vertebrate protein. In some embodiments, the protein is a recombinant protein. In one embodiment, the protein is a recombinant protein. In one embodiment, the recombinant protein is a recombinant human protein.

In one embodiment, the present invention provides a composition comprising an insulin protein and an omega-3 fatty acid. As provided herein (Examples), such compositions have utility in the oral administration of insulin, whereby the insulin is absorbed by the intestines into the bloodstream in an active form.

In another embodiment, the present invention provides a composition comprising a protein with enzymatic activity and an omega-3 fatty acid.

In one embodiment, the insulin of methods and compositions of the present invention is human insulin. In another embodiment, the insulin is a recombinant insulin. In another embodiment, the insulin is recombinant human insulin. In another embodiment, the insulin is bovine insulin. In another embodiment, the insulin is porcine insulin. In another embodiment, the insulin is whale insulin. In another embodiment, the insulin is a metal complex of insulin (e.g. a zinc complex of insulin, protamine zinc insulin, or globin zinc).

In another embodiment, the insulin is regular insulin. In another embodiment, the insulin is fast-acting insulin. In another embodinent, the insulin is lente insulin. In another embodiment, the insulin is semilente insulin. In another embodiment, the insulin is Ultralente insulin. In another embodiment, the insulin is NPH insulin. In another embodiment, the insulin is glargine insulin. In another embodiment, the insulin is lispro insulin. In another embodiment, the insulin is aspart insulin. In another embodiment, the insulin is a combination of two or more of any of the above types of insulin. In another embodiment, the insulin is any other type of insulin known in the art. Each possibility represents a separate embodiment of the present invention.

In one embodiment, the amount of insulin utilized in methods and compositions of the present invention is 0.5-3 units (u)/kg in humans. In one embodiment, the units used to measure insulin in methods and compositions of the present invention are USP Insulin Units. In one embodiment, the units used to measure insulin are milligrams. In another embodiment, one USP Insulin Unit is equivalent to 45.5 mg insulin.

In another embodiment, the amount of insulin is 0.1-1 u/kg. In another embodiment, the amount is 0.2-1 u/kg. In another embodiment, the amount is 0.3-1 u/kg. In another embodiment, the amount is 0.5-1 u/kg. In another embodiment, the amount is 0.1-2 u/kg. In another embodiment, the amount is 0.2-2 u/kg. In another embodiment, the amount is 0.3-2 u/kg. In another embodiment, the amount is 0.5-2 u/kg. In another embodiment, the amount is 0.7-2 u/kg. In another embodiment, the amount is 1-2 u/kg. In another embodiment, the amount is 1.2-2 u/kg. In another embodiment, the amount is 1-1.2 u/kg. In another embodiment, the amount is 1-1.5 u/kg. In another embodiment, the amount is 1-2.5 u/kg. In another embodiment, the amount is 1-3 u/kg. In another embodiment, the amount is 2-3 u/kg. In another embodiment, the amount is 1-5 u/kg. In another embodiment, the amount is 2-5 u/kg. In another embodiment, the amount is 3-5 u/kg.

In another embodiment, the amount of insulin is 0.1 u/kg. In another embodiment, the amount is 0.2 u/kg. In another embodiment, the amount is 0.3 u/kg. In another embodiment, the amount is 0.4 u/kg. In another embodiment, the amount is 0.5 u/kg. In another embodiment, the amount is 0.6 u/kg. In another embodiment, the amount is 0.8 u/kg. In another embodiment, the amount is 1 u/kg. In another embodiment, the amount is 1.2 u/kg. In another embodiment, the amount is 1.4 u/kg. In another embodiment, the amount is 1.6 u/kg. In another embodiment, the amount is 1.8 u/kg. In another embodiment, the amount is 2 u/kg. In another embodiment, the amount is 2.2 u/kg. In another embodiment, the amount is 2.5 u/kg. In another embodiment, the amount is 3 u/kg.

In another embodiment, the amount of insulin is 1-10 u. In another embodiment, the amount is 2-10 u. In another embodiment, the amount is 3-10 u. In another embodiment, the amount is 5-10 u. In another embodiment, the amount is 1-20 u. In another embodiment, the amount is 2-20 u. In another embodiment, the amount is 3-20 u. In another embodiment; the amount is 5-20 u. In another embodiment, the amount is 7-20 u. In another embodiment, the amount is 10-20 u. In another embodiment, the amount is 12-20 u. In another embodiment, the amount is 10-12 u. In another embodiment, the amount is 10-15 u. In another embodiment, the amount is 10-25 u. In another embodiment, the amount is 10-30 u. In another embodiment, the amount is 20-30 u. In another embodiment, the amount is 10-50 u. In another embodiment, the amount is 20-50 u. In another embodiment, the amount is 30-50 u. In another embodiment, the amount is 20-100 u. In another embodiment, the amount is 30-100 u. In another embodiment, the amount is 100-150 u. In another embodiment, the amount is 100-250 u. In another embodiment, the amount is 100-300 u. In another embodiment, the amount is 200-300 u. In another embodiment, the amount is 100-500 u. In another embodiment, the amount is 200-500 u. In another embodiment, the amount is 300-500 u. In another embodiment, the amount is 200-1000 u. In another embodiment, the amount is 300-1000 u.

In another embodiment, the amount of insulin is 1 u. In another embodiment, the amount is 2 u. In another embodiment, the amount is 3 u. In another embodiment, the amount is 4 u. In another embodiment, the amount is 5 u. In another embodiment, the amount is 6 u. In another embodiment, the amount is 8 u. In another embodiment, the amount is 10 u. In another embodiment, the amount is 12 u. In another embodiment, the amount is 14 u. In another embodiment, the amount is 16 u. In another embodiment, the amount is 18 u. In another embodiment, the amount is 20 u. In another embodiment, the amount is 22 u. In another embodiment, the amount is 25 u. In another embodiment, the amount is 30 u. In another embodiment, the amount is 50 u. In another embodiment, the amount is 80 u. In another embodiment, the amount is 100 u. In another embodiment, the amount is 120 u. In another embodiment, the amount is 140 u. In another embodiment, the amount is 160 u. In another embodiment, the amount is 180 u. In another embodiment, the amount is 200 u. In another embodiment, the amount is 300 u. In another embodiment, the amount is 500 u.

In another embodiment, the use of sustained release dosage forms (e.g. sustained release microencapsulation) enables the treatment frequency to be reduced to once or twice a day. In another embodiment, the insulin dosage is increased correspondingly with decreasing frequency of administration.

Each amount of insulin represents a separate embodiment of the present invention.

Methods of measuring insulin levels are well known in the art. In one embodiment, levels of recombinant insulin are measuring using a human insulin radio-immunoassay (RIA) kit, e.g. the kit manufactured by Linco Research Inc, (St. Charles, Mo.). In another embodiment, levels of C peptide are measured as well, to determine the relative contributions of endogenous and exogenous insulin to observed rises in insulin levels. In another embodiment, insulin ELISA kits are used. In another embodiment, insulin levels are measured by any other method known in the art. Each possibility represents a separate embodiment of the present invention.

In some embodiments, oinega-3 fatty acid can be found in vegetable sources such as the seeds of chia, perilla, flax, walnuts, purslane, lingonberry, seabuckthom, and hemp. In some embodiments, omega-3 fatty acids can also be found in the fruit of the acai palm. In another embodiment, the omega-3 fatty acid has been provided in the form of a synthetic omega-3 fatty acid. In one embodiment, the omega-3 fatty acid of methods and compositions of the present invention has been provided to the composition in the form of a fish oil. In another embodiment, the omega-3 fatty acid has been provided in the form of canola oil. In another embodiment, the omega-3 fatty acid has been provided in the form of flaxseed oil. In another embodiment, the omega-3 fatty acid has been provided in the form of any other omega-3 fatty acid-rich source known in the art. In another embodiment, the omega-3 fatty acid has been provided in the form of a synthetic omega-3 fatty acid. Each form of omega-3 fatty acids represents a separate embodiment of the present invention.

In another embodiment, the omega-3 fatty acid of methods and compositions of the present invention is an omega-3 polyunsaturated fatty acid. In another embodiment, the omega-3 fatty acid is DHA, an omega-3, polyunsaturated, 22-carbon fatty acid also referred to as 4,7,10,13,16,19-docosahexaenoic acid. In another embodiment, the omega-3 fatty acid is α-linolenic acid (9,12,15-octadecatrienoic acid). In another embodiment, the omega-3 fatty acid is stearidonic acid (6, 9, 12, 15-octadecatetraenoic acid). In another embodiment, the omega-3 fatty acid is eicosatrienoic acid (ETA; 11,14,17-eicosatrienoic acid). In another embodiment, the omega-3 fatty acid is eicsoatetraenoic acid (8,11,14,17-eicosatetraenoic acid). In one embodiment, the omega-3 fatty acid is eicosapentaenoic acid (EPA; 5,8,11,14,17-eicosapentaenoic acid). In another embodiment, the omega-3 fatty acid is eicosahexaenoic acid (also referred to as "EPA"; 5,7,9,11, 14,17-eicosahexaenoic acid). In another embodiment, the omega-3 fatty acid is docosapentaenoic acid (DPA; 7,10,13, 16,19-docosapenatenoic acid). In another embodiment, the omega-3 fatty acid is tetracosahexaenoic acid (6,9,12,15,18, 21-tetracosahexaenoic acid). In another embodiment, the omega-3 fatty acid is any other omega-3 fatty acid known in the art. Each omega-3 fatty acid represents a separate embodiment of the present invention.

In another embodiment, compositions of the present invention further comprise an inhibitor of a protease. As provided herein, protease inhibitors enhance the ability of omega-3 fatty acids to protect insulin and facilitate its absorption in the intestine.

In some embodiments, protease inhibitor inhibits the function of peptidases. In one embodiment, protease inhibitors enhance the ability of omega-3 fatty acids to protect the protein of the present invention and facilitate its absorption in the intestine. In some embodiments, the protease inhibitor of the present invention is a protein. In some embodiments, protease inhibitors comprise cysteine protease inhibitors, serine protease inhibitors (serpins), trypsin inhibitors, threonine protease inhibitors, aspartic protease inhibitors, metallo protease inhibitors. In some embodiments, protease inhibitors comprise suicide inhibitor, transition state inhibitor, or chelating agents.

In one embodiment, the protease inhibitor is soybean trypsin inhibitor (SBTI). In another embodiment, the protease inhibitor is AEBSF-HCl. In another embodiment, the inhibitor is (epsilon)-aminocaproic acid. In another embodiment, the inhibitor is (alpha) 1-antichymotypsin. In another embodiment, the inhibitor is antipain. In another embodiment, the inhibitor is antithrombin m. In another embodiment, the inhibitor is (alpha) 1-antitrypsin ([alpha] 1-proteinase inhibitor). In another embodiment, the inhibitor is APMSF-HCl (4-amidinophenyl-methane sulfonyl-fluoride). In another embodiment, the inhibitor is sprotinin. In another embodiment, the inhibitor is benzamidine-HCl. In another embodiment, the inhibitor is chymostatin. In another embodiment, the inhibitor is DFP (diisopropylfluoro-phosphate). In another embodiment, the inhibitor is leupeptin. In another embodiment, the inhibitor is PEFABLOC® SC (4-(2-Aminoethyl)-benzenesulfonyl fluoride hydrochloride). In another embodiment, the inhibitor is PMSF (phenylmethyl sulfonyl fluoride). In another embodiment, the inhibitor is TLCK (1-Chloro-3-tosylamido-7-amino-2-heptanone HCl). In another embodiment, the inhibitor is TPCK (1-Chloro-3-tosylamido-4-phenyl-2-butanone). In another embodiment, the inhibitor is trypsin inhibitor from egg white (Ovomucoid). In another embodiment, the inhibitor is trypsin inhibitor from soybean. In another embodiment, the inhibitor is aprotinin. In another embodiment, the inhibitor is pentamidine isethionate. In another embodiment, the inhibitor is pepstatin. In another embodiment, the inhibitor is guanidium. In another embodiment, the inhibitor is alpha 2-macroglobulin. In another embodiment, the inhibitor is a chelating agent of zinc. In another embodiment, the inhibitor is iodoacetate. In another embodiment, the inhibitor is zinc. Each possibility represents a separate embodiment of the present invention.

In another embodiment, the amount of protease inhibitor utilized in methods and compositions of the present invention is 0.1 mg/dosage unit. In another embodiment, the amount of protease inhibitor is 0.2 mg/dosage unit. In another embodiment, the amount is 0.3 mg/dosage unit. In another embodiment, the amount is 0.4 mg/dosage unit. In another embodiment, the amount is 0.6 mg/dosage unit. In another embodiment, the amount is 0.8 mg/dosage unit. In another embodiment, the amount is 1 mg/dosage unit. In another embodiment, the amount is 1.5 mg/dosage unit. In another embodiment, the amount is 2 mg/dosage unit. In another embodiment, the amount is 2.5 mg/dosage unit. In another embodiment, the amount is 3 mg/dosage unit. In another embodiment, the amount is 5 mg/dosage unit. In another embodiment, the amount is 7 mg/dosage unit. In another embodiment, the amount is 10 mg/dosage unit. In another embodiment, the amount is 12 mg/dosage unit. In another embodiment, the amount is 15 mg/dosage unit. In another embodiment, the amount is 20 mg/dosage unit. In another embodiment, the amount is 30 mg/dosage unit. In another embodiment, the amount is 50 mg/dosage unit. In another embodiment, the amount is 70 mg/dosage unit. In another embodiment, the amount is 100 mg/dosage unit.

In another embodiment, the amount of protease inhibitor is 0.1-1 mg/dosage unit. In another embodiment, the amount of protease inhibitor is 0.2-1 mg/dosage unit. In another embodiment, the amount is 0.3-1 mg/dosage unit. In another embodiment, the amount is 0.5-1 mg/dosage unit. In another embodiment, the amount is 0.1-2 mg/dosage unit. In another embodiment, the amount is 0.2-2 mg/dosage unit. In another embodiment, the amount is 0.3-2 mg/dosage unit. In another embodiment, the amount is 0.5-2 mg/dosage unit. In another embodiment, the amount is 1-2 mg/dosage unit. In another embodiment, the amount is 1-10 mg/dosage unit. In another embodiment, the amount is 2-10 mg/dosage unit. In another embodiment, the amount is 3-10 mg/dosage unit. In another embodiment, the amount is 5-10 mg/dosage unit. In another embodiment, the amount is 1-20 mg/dosage unit. In another embodiment, the amount is 2-20 mg/dosage unit. In another embodiment, the amount is 3-20 mg/dosage unit. In another embodiment, the amount is 5-20 mg/dosage unit. In another embodiment, the amount is 10-20 mg/dosage unit. In another-embodiment, the amount is 10-100 mg/dosage unit. In another embodiment, the amount is 20-100 mg/dosage unit. In another embodiment, the amount is 30-100 mg/dosage unit. In another embodiment, the amount is 50-100 mg/dosage unit. In another embodiment, the amount is 10-200 mg/dosage unit. In another embodiment, the amount is 20-200 mg/dosage unit. In another embodiment, the amount is 30-200 mg/dosage unit. In another embodiment, the amount is 50-200 mg/dosage unit. In another embodiment, the amount is 100-200 mg/dosage unit.

In another embodiment, the amount of protease inhibitor utilized in methods and compositions of the present invention is 1000 k.i.u. (kallikrein inactivator units)/pill. In another embodiment, the amount is 10 k.i.u./dosage unit. In another embodiment, the amount is 12 k.i.u./dosage unit. In another embodiment, the amount is 15 k.i.u./dosage unit. In another embodiment, the amount is 20 k.i.u./dosage unit. In another embodiment, the amount is 30 k.i.u./dosage unit. In another embodiment, the amount is 40 k.i.u./dosage unit. In another embodiment, the amount is 50 k.i.u./dosage unit. In another embodiment, the amount is 70 k.i.u./dosage unit. In another embodiment, the amount is 100 k.i.u./dosage unit. In another embodiment, the amount is 150 k.i.u./dosage unit. In another embodiment, the amount is 200 k.i.u./dosage unit. In another embodiment, the amount is 300 k.i.u./dosage unit. In another embodiment, the amount is 500 k.i.u./dosage unit. In another embodiment, the amount is 700 k.i.u./dosage unit. In another embodiment, the amount is 1500 k.i.u./dosage unit. In another embodiment, the amount is 3000 k.i.u./dosage unit. In another embodiment, the amount is 4000 k.i.u./dosage unit. In another embodiment, the amount is 5000 k.i.u./dosage unit.

Each amount of protease inhibitor represents a separate embodiment of the present invention.

In another embodiment, the protease targeted by the protease inhibitor of methods and compositions of the present invention is a serine protease. In another embodiment, the protease is trypsin. In another embodiment, the protease is chymotrypsin. In another embodiment, the protease is carboxypeptidase. In another embodiment, the protease is aminopeptidase. In another embodiment, the protease is any other protease that functions in the duodenum or the small intestine. Each possibility represents a separate embodiment of the present invention.

In another embodiment, compositions of the present invention further comprise a substance that enhances absorption of the insulin through an intestinal mucosal barrier. Such a substance is referred to herein as an "enhancer." As provided herein, enhancers, when used together with omega-3 fatty acids, enhance the ability of insulin to be absorbed in the intestine.

In one embodiment, the enhancer is didecanoylphosphatidylcholine (DDPC). In one embodiment, the enhancer is a chelating agent such as ethylenediaminetetraacetic acid (EDTA) or egtazic acid EGTA. In a preferred embodiment, EDTA is sodium-EDTA. In some embodiments, the enhancer is NO donor. In some embodiments, the enhancer is a bile acid, glycine-conjugated form of a bile acid, or an alkali metal salt. In one embodiment, absorption enhancement is achieved through utilization of a combination of $\alpha$-galactosidase and $\beta$-mannanase. In some embodiments, the enhancer is a fatty acid such as sodium caprate. In one embodiment, the enhancer is sodium glycocholate. In one embodiment, the enhancer is sodium salicylate. In one embodiment, the enhancer is n-dodecyl-$\beta$-D-maltopyranoside. In some embodiments, surfactants serve as absorption enhancer. In one embodiment, the enhancer is chitisan such as N,N,N-trimethyl chitosan chloride (TMC).

In one embodiment, NO donors of the present invention comprise 3-(2-Hydroxy-1-(1-methylethyl)-2-nitrosohydrazino)-1-propanamine, N-ethyl-2-(1-ethyl-hydroxy-2-nitrosohydrazino)-ethanamine, or S-Nitroso-N-acetylpenicillamine In another embodiment, the bile acid is cholic acid. In another embodiment, the bile acid is chenodeoxycholic acid. In another embodiment, the bile acid is taurocholic acid. In another embodiment, the bile acid is taurochenodeoxycholic acid. In another embodiment, the bile acid is glycocholic acid. In another embodiment, the bile acid is glycochenocholic acid. In another embodiment, the bile acid is 3 beta-monohydroxychloric acid. In another embodiment, the bile acid is lithocholic acid. In another embodiment, the bile acid is 5 beta-cholanic acid. In another embodiment, the bile acid is 3,12-diol-7-one-5 beta-cholanic acid. In another embodiment, the bile acid is 3 alpha-hydroxy-12-ketocholic acid. In another embodiment, the bile acid is 3 beta-hydroxy-12-ketocholic acid. In another embodiment, the bile acid is 12 alpha-3 beta-dihydrocholic acid. In another embodiment, the bile acid is ursodesoxycholic acid.

In one embodiment, the enhancer is a nonionic surfactant. In one embodiment, the enhancer is a nonionic polyoxyethylene ether surface active agent (e.g one having an HLB value of 6 to 19, wherein the average number of polyoxyethylene units is 4 to 30). In another embodiment, the enhancer is an anionic surface active agents. In another embodiment, the enhancer is a cationic surface active agent. In another embodiment, the enhancer is an ampholytic surface active agent. In one embodiment, zwitteruionic surfactants such as acylcarnitines serve as absorption enhancers.

In another embodiment, the amount of enhancer utilized in methods and compositions of the present invention is 0.1 mg/dosage unit. In another embodiment, the amount of enhancer is 0.2 mg/dosage unit. In another embodiment, the amount is 0.3 mg/dosage unit. In another embodiment, the amount is 0.4 mg/dosage unit. In another embodiment, the amount is 0.6 mg/dosage unit. In another embodiment, the amount is 0.8 mg/dosage unit. In another embodiment, the amount is 1 mg/dosage unit. In another embodiment, the amount is 1.5 mg/dosage unit. In another embodiment, the amount is 2 mg/dosage unit. In another embodiment, the amount is 2.5 mg/dosage unit. In another embodiment, the amount is 3 mg/dosage unit. In another embodiment, the amount is 5 mg/dosage unit. In another embodiment, the amount is 7 mg/dosage unit. In another embodiment, the amount is 10 mg/dosage unit. In another embodiment, the amount is 12 mg/dosage unit. In another embodiment, the amount is 15 mg/dosage unit. In another embodiment, the amount is 20 mg/dosage unit. In another embodiment, the amount is 30 mg/dosage unit. In another embodiment, the amount is 50 mg/dosage unit. In another embodiment, the amount is 70 mg/dosage unit. In another embodiment, the amount is 100 mg/dosage unit.

In another embodiment, the amount of enhancer is 0.1-1 mg/dosage unit. In another embodiment, the amount of enhancer is 0.2-1 mg/dosage unit. In another embodiment, the amount is 0.3-1 mg/dosage unit. In another embodiment, the amount is 0.5-1 mg/dosage unit. In another embodiment, the amount is 0.1-2 mg/dosage unit. In another embodiment, the amount is 0.2-2 mg/dosage unit. In another embodiment, the amount is 0.3-2 mg/dosage unit. In another embodiment, the amount is 0.5-2 mg/dosage unit. In another embodiment, the amount is 1-2 mg/dosage unit. In another embodiment, the amount is 1-10 mg/dosage unit. In another embodiment, the amount is 2-10 mg/dosage unit. In another embodiment, the amount is 3-10 mg/dosage unit. In another embodiment, the amount is 5-10 mg/dosage unit. In another embodiment, the amount is 1-20 mg/dosage unit. In another embodiment, the amount is 2-20 mg/dosage unit. In another embodiment, the amount is 3-20 mg/dosage unit. In another embodiment, the amount is 5-20 mg/dosage unit. In another embodiment, the amount is 10-20 mg/dosage unit. In another embodiment, the amount is 10-100 mg/dosage unit. In another embodiment, the amount is 20-100 mg/dosage unit. In another embodiment, the amount is 30-100 mg/dosage unit. In another embodiment, the amount is 50-100 mg/dosage unit. In another embodiment, the amount is 10-200 mg/dosage unit. In another embodiment, the amount is 20-200 mg/dosage unit. In another embodiment, the amount is 30-200 mg/dosage unit. In another embodiment, the amount is 50-200 mg/dosage unit. In another embodiment, the amount is 100-200 mg/dosage unit.

Each type and amount of enhancer represents a separate embodiment of the present invention.

In another embodiment, compositions of the present invention further comprise a coating that inhibits digestion of the composition in the stomach of a subject.

In one embodiment, coating inhibits digestion of the composition in the stomach of a subject. In one embodiment, the coated dosage forms of the present invention release drug when pH move towards alkaline range. In one embodiment, coating is a monolayer, wherein in other embodiments coating applied in multilayers. In one embodiment, coating is a bioadhesive polymer that selectively binds the intestinal mucosa and thus enables drug release in the attachment site. In one embodiment, the enteric coating is an enteric film coating. In some embodiment, coating comprises biodegradable polysaccharide, chitosan, aquateric aqueous, aquacoat ECD, azo polymer, cellulose acetate phthalate, cellulose acetate trimelliate, hydroxypropylmethyl cellulose phthalate, gelatin, poly vinyl acetate phthalate, hydrogel, pulsincap, or a combination thereof. In one embodiment, pH sensitive coating will be used according to the desired release site and/or profile as known to one skilled in the art.

In one embodiment, the coating is an enteric coating. Methods for enteric coating are well known in the art, and are described, for example, in Siepmann F, Siepmann J et al, Blends of aqueous polymer dispersions used for pellet coating: importance of the particle size. J Control Release 2005; 105 (3): 226-39; and Huyghebaert N, Vermeire A, Remon J P. In vitro evaluation of coating polymers for enteric coating and human ileal targeting. Int J Pharm 2005; 298 (1): 26-37. Each method represents a separate embodiment of the present invention.

In another embodiment, Eudragit®, an acrylic polymer, is used as the enteric coating. The use of acrylic polymers for the coating of pharmaceutical preparations is well known in the art. Eudragit Acrylic Polymers have been shown to be safe, and are neither absorbed nor metabolized by the body, but rather are eliminated.

In another embodiment, the coating is a gelatin coating. In another embodiment, microencapsulation is used to protect the insulin against decomposition in the stomach. Methods for applying a gelatin coating and for microencapsulation are well known in the art. Each method represents a separate embodiment of the present invention.

In another embodiment, the coating is a film-coating. In another embodiment, the coating is ethylcellulose. In another embodiment, the coating is a water-based dispersion of ethylcellulose, e.g. hydroxypropylmethylcelullose (HPMC) E15. In another embodiment, the coating is a gastro-resistant coatings, e.g. a polymer containing carboxylic acid groups as a functional moiety. In another embodiment, the coating is a monolithic matrix. In another embodiment, the coating is a cellulose ether (e.g. hypromellose (HPMC). Each type of coating represents a separate embodiment of the present invention.

In another embodiment, a multiparticulate dosage forms is used to inhibit digestion of the composition in the stomach.

Each type of coating, dosage form, etc, that inhibits digestion of the composition in the stomach represents a separate embodiment of the present invention.

In another embodiment, the present invention provides a method for oral administration of a protein with an enzymatic activity to a subject, whereby a substantial fraction of the protein retains the enzymatic activity after absorption through an intestinal mucosal barrier of the subject, comprising administering orally to the subject a pharmaceutical composition comprising the protein and an omega-3 fatty acid, thereby orally administering a protein with an enzymatic activity to a subject.

In one embodiment, the protein is a recombinant protein. In one embodiment, the protein is an insulin. In another embodiment, the protein is a glucagon. In another embodiment, the protein is an interferon gamma. In another embodiment, the protein is an interferon alpha. In another embodiment, the protein is a growth hormone. In another embodiment, the protein is an erythropoietin. In another embodiment, the protein is granulocyte colony stimulating factor (G-CSF). In another embodiment, the protein is any other protein known in the art.

In another embodiment, the protein is a growth hormone. In one embodiment, the growth hormone is somatotropin. In another embodiment, the growth hormone is Insulin Growth Factor-I (IGF-I). In another embodiment, the growth hormone is any other growth hormone known in the art.

In another embodiment, the protein has a molecular weight (MW) of 1-50 kilodalton (kDa). In another embodiment, the MW is 1-45 kDa. In another embodiment, the MW is 1-40 kDa. In another embodiment, the MW is 1-35 kDa. In another embodiment, the MW is 1-30 kDa. In another embodiment, the MW is 1-25 kDa. In another embodiment, the MW is 1-20 kDa. In another embodiment, the MW is 10-50 kDa. In another embodiment, the MW is 15-50 kDa. In another embodiment, the MW is 20-50 kDa. In another embodiment, the MW is 25-50 kDa. In another embodiment, the MW is 30-50 kDa. In another embodiment, the MW is 35-50 kDa. In another embodiment, the MW is 1-100 kDa. In another embodiment, the MW is 1-90 kDa. In another embodiment, the MW is 1-80 kDa. In another embodiment, the MW is 1-70 kDa. In another embodiment, the MW is 1-60 kDa. In another embodiment, the MW is 10-100 kDa. In another embodiment, the MW is 15-100 kDa. In another embodiment, the MW is 20-100 kDa. In another embodiment, the MW is 25-100 kDa. In another embodiment, the MW is 30-100 kDa. In another embodiment, the MW is 10-80 kDa. In another embodiment, the MW is 15-80 kDa. In another embodiment, the MW is 20-80 kDa. In another embodiment, the MW is 25-80 kDa. In another embodiment, the MW is 30-80 kDa. Each possibility represents a separate embodiment of the present invention.

In another embodiment, the MW is less than 20 kDa. In another embodiment, the MW is less than 25 kDa. In another embodiment, the MW is less than 30 kDa. In another embodiment, the MW is less than 35 kDa. In another embodiment, the MW is less than 40 kDa. In another embodiment, the MW is less than 45 kDa. In another embodiment, the MW is less than 50 kDa. In another embodiment, the MW is less than 55 kDa. In another embodiment, the MW is less than 60 kDa. In another embodiment, the MW is less than 65 kDa. In another embodiment, the MW is less than 70 kDa. In another embodiment, the MW is less than 75 kDa. In another embodiment, the MW is less than 80 kDa. In another embodiment, the MW is less than 85 kDa. In another embodiment, the MW is less than 90 kDa. In another embodiment, the MW is less than 95 kDa. In another embodiment, the MW is less than 100 kDa.

The molecular weights of some of the proteins mentioned above are as follows: insulin—6 kilodalton (kDa); glucagon—3.5 kDa; interferon, 28 kDa, growth hormone—21.5-47 kDa; human serum albumin—69 kDa; erythropoietin—34 kDa; G-CSF—30-34 kDa. Thus, in one embodiment, the molecular weight of these proteins is appropriate for administration by methods of the present invention.

In another embodiment, methods and compositions of the present invention are used to administer a human serum albumin. Human serum albumin is not, in one embodiment, considered to be a pharmaceutically-active component; however, it can be used in the context of the present invention as a therapeutically-beneficial carrier for an active component.

Each type of protein represents a separate embodiment of the present invention.

In another embodiment, the present invention provides a method for treating diabetes mellitus in a subject, comprising administering orally to the subject a pharmaceutical composition comprising an insulin and an omega-3 fatty acid, thereby treating diabetes mellitus.

In one embodiment, the diabetes mellitus is Type I diabetes. In another embodiment, the diabetes mellitus is Type II diabetes. In another embodiment, the diabetes mellitus is insulin-dependent diabetes. In another embodiment, the diabetes mellitus is non-insulin-dependent diabetes. In another embodiment, the diabetes mellitus is any other type of diabetes known in the art. Each possibility represents a separate embodiment of the present invention.

In one embodiment, three treatments a day of the insulin composition are administered. In another embodiment, two treatments a day are administered. In another embodiment, four treatments a day are administered. In another embodiment, one treatment a day is administered. In another embodiment, more than four treatments a day are administered. Each possibility represents a separate embodiment of the present invention.

Any of the methods of the present invention may utilize, in various embodiments, any of the compositions of the present invention.

In another embodiment, the present invention provides a composition for oral administration of insulin, comprising an insulin protein and an omega-3 fatty acid, whereby a substantial fraction of the insulin retains the enzymatic activity after absorption through an intestinal mucosal barrier of the subject.

In one embodiment, the present invention provides a composition for oral administration of a protein, comprising a protein and an omega-3 fatty acid, whereby a substantial fraction of the protein retains the enzymatic activity after absorption through an intestinal mucosal barrier of the subject.

In one embodiment, the present invention provides the use of a protein and an omega-3 fatty acid in the manufacture of a medicament for oral administration of a protein with an enzymatic activity to a subject, whereby a substantial fraction of the protein retains the enzymatic activity after absorption through an intestinal mucosal barrier of the subject.

In one embodiment, the present invention provides the use of an insulin protein and an omega-3 fatty acid in the manufacture of a medicament for treating diabetes mellitus in a subject.

In one embodiment, methods and compositions of the present invention have the advantage of more closely mimicking physiological insulin secretion by the pancreas. When insulin is secreted into the portal vein, the liver is exposed to a greater insulin concentration than peripheral tissues. Similarly, insulin administered according to the present invention reaches the intestine and is absorbed in the body through the intestine and through the portal system to the liver. This absorption route thus resembles the physiological secretion of insulin by the pancreas, enabling, in this embodiment, delicate control of the blood glucose level and the metabolic activities of the liver and the peripheral organs controlled by insulin. By contrast, when insulin is administered to insulin-deficient diabetic patients via the peripheral venous system, the concentration of insulin in the portal vein is similar to that in the peripheral circulation, resulting in hypoinsulinemia in the portal vein and the liver and hyperinsulinemia in the peripheral venous system. This leads, in one embodiment, to an abnormal pattern of glucose disposal.

In another embodiment, different constituents of compositions of the present composition are absorbed at different rates from the intestinal lumen into the blood stream. The absorption of the bile acid, in one embodiment, is significantly faster than the absorption of insulin.

For this reason, in another embodiment, a drug regimen involving ingestion of a pair of pills at spaced intervals, e.g., a second pill containing a higher concentration of enhancer is taken at a defined interval (e.g. 30 minutes) after the first pill. In another embodiment, certain of the constituents are microencapsulated to enhance the absorption of the insulin into the system.

In one embodiment, a treatment protocol of the present invention is therapeutic. In another embodiment, the protocol is prophylactic. Each possibility represents a separate embodiment of the present invention.

In another embodiment, solid carriers/diluents for use in methods and compositions of the present invention include, but are not limited to, a gum, a starch (e.g. corn starch, pregeletanized starch), a sugar (e.g., lactose, mannitol, sucrose, dextrose), a cellulosic material (e.g. microcrystalline cellulose), an acrylate (e.g. polymethylacrylate), calcium carbonate, magnesium oxide, talc, or mixtures thereof.

In another embodiment, the compositions further comprise binders (e.g. acacia, cornstarch, gelatin, carbomer, ethyl cellulose, guar gum, hydroxypropyl cellulose, hydroxypropyl methyl cellulose, povidone), disintegrating agents (e.g. cornstarch, potato starch, alginic acid, silicon dioxide, croscarmelose sodium, crospovidone, guar gum, sodium starch glycolate), buffers (e.g., Tris-HCI, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., glycerol, polyethylene glycerol), anti-oxidants (e.g., ascorbic acid, sodium metabisulfite, butylated hydroxyanisole), stabilizers (e.g. hydroxypropyl cellulose, hyroxypropylmethyl cellulose), viscosity increasing agents (e.g. carbomer, colloidal silicon dioxide, ethyl cellulose, guar gum), sweeteners (e.g. aspartame, citric acid), preservatives (e.g., Thimerosal, benzyl alcohol, parabens), lubricants (e.g. stearic acid, magnesium stearate, polyethylene glycol, sodium lauryl sulfate), flow-aids (e.g. colloidal silicon dioxide), plasticizers (e.g. diethyl phthalate, triethyl citrate), emulsifiers (e.g. carbomer, hydroxypropyl cellulose, sodium lauryl sulfate), polymer coatings (e.g., poloxamers or poloxamines), coating and film forming agents (e.g. ethyl cellulose, acrylates, polymethacrylates) and/or adjuvants. Each of the above excipients represents a separate embodiment of the present invention.

In some embodiments, the dosage forms of the present invention are formulated to achieve an immediate release profile, an extended release profile, or a delayed release profile. In some embodiments, the release profile of the composition is determined by using specific excipients that serve for example as binders, disintegrants, fillers, or coating materials. In one embodiment, the composition will be formulated to achieve a particular release profile as known to one skilled in the art.

In one embodiment, the composition is formulated as an oral dosage form. In one embodiment, the composition is a solid oral dosage form comprising tablets, chewable tablets, or capsules. In one embodiment the capsules are soft gelatin capsules.

In other embodiments, controlled- or sustained-release coatings utilized in methods and compositions of the present invention include formulation in lipophilic depots (e.g. fatty acids, waxes, oils).

The compositions also include, in another embodiment, incorporation of the active material into or onto particulate preparations of polymeric compounds such as polylactic acid, polglycolic acid, hydrogels, etc, or onto liposomes, microemulsions, micelles, unilamellar or multilamellar vesicles, erythrocyte ghosts, or spheroplasts.) Such compositions will influence the physical state, solubility, stability, rate of in vivo release, and rate of in vivo clearance. In another embodiment, particulate compositions of the active ingredients are coated with polymers (e.g. poloxamers or poloxarnines)

In another embodiment, the compositions containing the insulin and omega-3 fatty acid are delivered in a vesicle, e.g. a liposome (see Langer, Science 249:1527-1533 (1990); Treat et al., in Liposomes in the Therapy of Infectious Disease and Cancer, Lopez-Berestein and Fidler (eds.), Liss, N.Y., pp. 353-365 (1989); Lopez-Berestein, ibid., pp. 317-327; see generally ibid).

The preparation of pharmaceutical compositions that contain an active component, for example by mixing, granulating, or tablet-forming processes, is well understood in the art. The active therapeutic ingredient is often mixed with excipients that are pharmaceutically acceptable and compatible with the active ingredient. For oral administration, the active ingredients of compositions of the present invention are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions.

Each of the above additives, excipients, formulations and methods of administration represents a separate embodiment of the present invention.

In one embodiment, the term "treating" refers to curing a disease. In another embodiment, "treating" refers to preventing a disease. In another embodiment, "treating" refers to reducing the incidence of a disease. In another embodiment, "treating" refers to ameliorating symptoms of a disease. In another embodiment, "treating" refers to inducing remission. In another embodiment, "treating" refers to slowing the progression of a disease.

EXPERIMENTAL DETAILS SECTION

Example 1

Protection of Insulin From Proteases And Successful Administration Via the Duodenum In Dogs Materials Ane Experimental Methods
Formulation The day of dosing, a formulation containing 100 milligram (mg) EDTA (Sigma-Aldrich, St. Louis, Mo.), 100 mg soybean trypsin inhibitor (SBTI; Sigma), 5 mg insulin (recombinant crystalline) dissolved in 2 milliliter (ml) fish oil was prepared and inserted into a transparent gelatin capsule.

Results

To test whether insulin can be protected from proteases and absorbed via the duodenum, a composition containing insulin, SBTI, EDTA, and fish oil was administered directly to the duodenum of an 8.8 kg beagle dog. Blood glucose was measured every 10 minutes following administration. As depicted below in Table 1, blood glucose levels were significantly reduced in response to the insulin.

Thus, compositions comprising an omega-3 fatty acid can protect insulin from proteases in the small intestine and enable direct absorption of orally administered insulin.

TABLE 1

Blood glucose concentrations following administration of insulin to the duodenum in experiment #1.

| Time (min) | Glucose in milligrams/deciliter (mg/dL) |
|---|---|
| −5 | 67 |
| 0 | 71 |
| 10 | 77 |
| 20 | 62 |
| 30 | 42 |
| 40 | 26 |
| 50 | 41 |
| 60 | 36 |
| 75 | 35 |
| 90 | 51 |
| 105 | 64 |
| 120 | 75 |

Example 2

Materials Ane Experimental Methods
Fonnulation 4 days prior to dosing, a formulation was prepared containing 125 mg EDTA, 100 mg SBTI, and 5 mg insulin in 2 ml fish oil in a gelatin capsule. The formulation was stored in the refrigerator (4° C.) until dosing.

Results

In the next experiment, a formulation of SBTI, EDTA, and fish oil was prepared 4 days prior to dosing, then administered directly to the duodenum of a 9.0 kg beagle dog. As depicted below in Table 2, blood glucose levels were significantly reduced in response to the insulin.

These results confirm the results of Example 1, showing that compositions comprising an omega-3 fatty acid can protect insulin from proteases in the small intestine and enable direct absorption of orally administered insulin. In addition, these results show that compositions of the present invention can be stored after constitution without losing potency.

TABLE 2

Blood glucose concentrations following administration of insulin to the duodenum in experiment #2.

| Time (min) | Glucose in milligrams/deciliter (mg/dL) |
| --- | --- |
| −5 | 69 |
| 0 | 68 |
| 10 | 64 |
| 20 | 38 |
| 30 | 19 |
| 40 | 31 |
| 50 | 39 |
| 60 | 55 |
| 75 | 66 |
| 90 | 75 |
| 105 | 75 |
| 120 | 73 |

Example 3

Oral Administration of Pills Containing Insulin And Omega-3 Fatty Acids

Preparation of Tablet Cores

Tablet cores comprising insulin and omega-3 fatty acids are prepared using methods well known in the art. For example, tablet cores may be prepared as described in Example 1.

Coating

The coating may be any delayed release coating known in the art. For example, the coating may be a polymer composed of the following ingredients:
  4 mg Eudragit L-100 (Polymer of Acrylic and Methacrylic Acid Esters)
  4 mg Talc NF
  0.4 mg Polyethylene Glycol 6000 NF In one embodiment, a solution of the enteric coated polymer is prepared by dissolving the polymer in a methylene chloride+isopropyl alcohol mixture. The tablets are coated by spraying the solution within a mildly warmed jar under constant agitation. The solvent vapors are continuously aspirated.

Measurement of Levels And Activity of Recombinant Insulin In Subjects' Plasma

A human insulin radio-immunoassay (RIA) kit (Linco Research Inc, St. Charles, Mo.) is used to measure levels of recombinant insulin. Levels of C peptide are measured as well, to determine the relative contributions of endogenous and exogenous insulin to observed rises in insulin levels.

Results

A mixture of EDTA, SBTI, and insulin dissolved in fish oil is formulated into tablet or capsule cores, coated with an enteric coating or gelatin coating, and administered to human subjects. Blood glucose levels of the subjects are measured periodically as described in the previous Examples. In addition, the subjects' plasma levels of recombinant insulin and its activity are tested. The coated pills are shown to deliver functional insulin to the subjects, and the insulin significantly lowers their blood glucose levels, showing that active insulin can be delivered to the bloodstream via oral administration. Different types of commercially available delayed release coatings are tested to determine which coating provides the best delivery of insulin, and this coating is used in subsequent Examples.

Example 4

Optimization of Source of Omega-3 Fatty Acids

Various omega-3 fatty acids or sources of omega-3 fatty acids (e.g. those listed above in the specification) are compared for their ability to preserve insulin following oral administration in methods and compositions of the present invention. Insulin tablets or capsules are formulated as described in the above Examples, except that the insulin is dissolved in the alternate source instead of in fish oil. The most effective source of omega-3 fatty acids is used in subsequent Examples.

Example 5

Optimization of Protease Inhibitors

Various protease inhibitors (either non-toxic or having an acceptable toxicity profile; e.g. those listed above in the specification) are compared for their ability to preserve insulin following oral administration in methods and compositions of the present invention. Insulin tablets or capsules are formulated as described in the above Examples, except that the alternate protease inhibitors are substituted for SBTI. Amounts of the protease inhibitors are also varied, to determine the optimal amounts. The most effective protease inhibitor/amount is used in subsequent Examples.

Example 6

Optimization of Enhancer

Various enhancers (e.g. those listed above in the specification) are compared for their ability to facilitate absorption of insulin following oral administration in methods and compositions of the present invention. Insulin tablets or capsules are formulated as described in the above Examples, except that the alternate enhancers are substituted for EDTA. Amounts of the enhancers are also varied, to determine the optimal amounts. The most effective enhancer/amount is used in subsequent experiments.

Example 7

Optimization of Type And Amount of Insulin

Various types and amounts of insulin e.g. those listed above in the specification) are compared for their ability to regulate blood sugar in methods and compositions of the present invention. Insulin tablets or capsules are formulated as described in the above Examples, except that the type and amount of insulin is varied. The most effective type/amount of insulin is used in clinical trials.

What is claimed is:

1. An oral dosage form for treating diabetes mellitus, comprising insulin, soybean trypsin inhibitor (SBTI), and EDTA, wherein said insulin, soybean trypsin inhibitor (SBTI), and EDTA are all in a water-free oily solution comprising an omega-3 fatty acid.

2. The oral dosage form of claim 1, wherein said insulin is recombinant insulin.

3. The oral dosage form of claim 1, wherein said oily solution is surrounded by a coating that inhibits digestion of said composition in a stomach of a subject.

4. The oral dosage form of claim 3, wherein said coating is an enteric coating.

5. The oral dosage form of claim 1, wherein said oily solution is surrounded by a gelatin coating.

6. The oral dosage form of claim 1, wherein said oily solution is the only liquid component of said oral dosage form.

7. The oral dosage form of claim 1, wherein the liquid phase of said oral dosage form consists of said insulin, said SBTI, said EDTA, and said oily solution.

8. A method for oral administration of insulin to a subject, comprising administering orally to said subject a pharmaceutical composition comprising said insulin, soybean trypsin inhibitor (SBTI), and EDTA, wherein said insulin, soybean trypsin inhibitor (SBTI), and EDTA are in a water-free oily solution comprising an omega-3 fatty acid.

9. The method of claim 8, wherein said insulin is recombinant insulin.

10. The method of claim 8, wherein said oily solution is surrounded by a coating that inhibits digestion of said composition in a stomach of a subject.

11. The method of claim 10, wherein said coating is an enteric coating.

12. The method of claim 8, wherein said oily solution is surrounded by a gelatin coating.

13. The method of claim 8, wherein said oily solution is the only liquid component of said oral dosage form.

14. The method of claim 8, wherein the liquid phase of said oral dosage form consists of said insulin, said SBTI, said EDTA, and said oily solution.

15. A method for treating diabetes mellitus in a subject, comprising administering orally to said subject a pharmaceutical composition comprising insulin, soybean trypsin inhibitor (SBTI), and EDTA, wherein said insulin, soybean trypsin inhibitor (SBTI), and EDTA are in a water-free oily solution comprising an omega-3 fatty acid, thereby treating diabetes mellitus.

16. The method of claim 15, wherein said insulin is a recombinant insulin.

17. The method of claim 15, wherein said oily solution is surrounded by a coating that inhibits digestion of said composition in a stomach of a subject.

18. The method of claim 17, wherein said coating is an enteric coating.

19. The method of claim 15, wherein said oily solution is surrounded by a gelatin coating.

20. The method of claim 15, wherein said oily solution is the only liquid component of said oral dosage form.

21. The method of claim 15, wherein the liquid phase of said oral dosage form consists of said insulin, said SBTI, said EDTA, and said oily solution.

22. The oral dosage form of claim 1, wherein said oral dosage form is non-alcoholic.

23. The method of claim 8, wherein said pharmaceutical composition is non-alcoholic.

24. The method of claim 15, wherein said pharmaceutical composition is non-alcoholic.

25. An oral dosage form for treating diabetes mellitus, comprising a therapeutic amount of insulin, soybean trypsin inhibitor (SBTI), and EDTA, wherein said insulin, soybean trypsin inhibitor (SBTI), and EDTA are all in a fish oil comprising an omega-3 fatty acid.

26. The oral dosage form of claim 25, wherein said insulin is recombinant insulin.

27. The oral dosage form of claim 25, wherein said fish oil is surrounded by a coating that inhibits digestion of said composition in a stomach of a subject.

28. The oral dosage form of claim 27, wherein said coating is an enteric coating.

29. The oral dosage form of claim 25, wherein said fish oil is surrounded by a gelatin coating.

30. The oral dosage form of claim 25, wherein said oral dosage form is non-aqueous and non-alcoholic.

31. The oral dosage form of claim 25, wherein said fish oil is the only liquid component of said oral dosage form.

32. A method for oral administration of insulin to a subject, comprising administering orally to said subject a pharmaceutical composition comprising a therapeutic amount of said insulin, soybean trypsin inhibitor (SBTI), and EDTA, in a fish oil comprising an omega-3 fatty acid.

33. The method of claim 32, wherein said insulin is recombinant insulin.

34. The method of claim 32, wherein said fish oil is surrounded by a coating that inhibits digestion of said composition in a stomach of a subject.

35. The method of claim 34, wherein said coating is an enteric coating.

36. The method of claim 32, wherein said fish oil is surrounded by a gelatin coating.

37. The method of claim 32, wherein said pharmaceutical composition is non-aqueous and non-alcoholic.

38. The method of claim 32, wherein said fish oil is the only liquid component of said oral dosage form.

39. A method for treating diabetes mellitus in a subject, comprising administering orally to said subject a pharmaceutical composition comprising a therapeutic amount of insulin, soybean trypsin inhibitor (SBTI), and EDTA, wherein said insulin, soybean trypsin inhibitor (SBTI), and EDTA are in a fish oil comprising an omega-3 fatty acid, thereby treating diabetes mellitus.

40. The method of claim 39, wherein said insulin is a recombinant insulin.

41. The method of claim 39, wherein said fish oil is surrounded by a coating that inhibits digestion of said composition in a stomach of a subject.

42. The method of claim 41, wherein said coating is an enteric coating.

43. The method of claim 39, wherein said fish oil is surrounded by a gelatin coating.

44. The method of claim 39, wherein said pharmaceutical composition is non-aqueous and non-alcoholic.

45. The method of claim 39, wherein said fish oil is the only liquid component of said oral dosage form.

* * * * *